(12) United States Patent
Huang et al.

(10) Patent No.: US 9,963,411 B2
(45) Date of Patent: May 8, 2018

(54) UTILIZATION AND RECYCLING OF EMITTED CARBON DIOXIDE

(71) Applicant: KING ABDULLAH UNIVERSITY OF SCIENCE AND TECHNOLOGY, Thuwal (SA)

(72) Inventors: Kuo-Wei Huang, Thuwal (SA); Amol Mahalingappa Hengne, Thuwal (SA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 0 days. days.

(21) Appl. No.: 15/368,201

(22) Filed: Dec. 2, 2016

(65) Prior Publication Data

US 2017/0158588 A1  Jun. 8, 2017

Related U.S. Application Data

(60) Provisional application No. 62/262,247, filed on Dec. 2, 2015.

(51) Int. Cl.
| | |
|---|---|
| *C07C 29/154* | (2006.01) |
| *C07C 41/01* | (2006.01) |
| *C07C 31/04* | (2006.01) |
| *C07C 43/04* | (2006.01) |
| *B01J 23/72* | (2006.01) |
| *B01J 23/80* | (2006.01) |
| *B01J 23/825* | (2006.01) |

(52) U.S. Cl.
CPC ........... *C07C 29/154* (2013.01); *B01J 23/72* (2013.01); *B01J 23/80* (2013.01); *B01J 23/825* (2013.01); *C07C 41/01* (2013.01)

(58) Field of Classification Search
CPC ....... C07C 29/154; C07C 41/01; C07C 31/04; C07C 43/043; B01J 23/825; B01J 23/72; B01J 23/80
See application file for complete search history.

(56) References Cited

U.S. PATENT DOCUMENTS

| | | |
|---|---|---|
| 5,928,806 A | 7/1999 | Olah |
| 7,459,590 B2 | 12/2008 | Olah |
| 7,608,743 B2 | 10/2009 | Olah |
| 8,212,088 B2 | 7/2012 | Olah |
| 8,596,047 B2 | 12/2013 | Shawabkeh |
| 9,327,986 B2 | 5/2016 | Guyomarc'h |
| 9,501,952 B2 | 11/2016 | Olah |

OTHER PUBLICATIONS

Toyir et al., Methanol synthesis from carbon dioxide and hydrogen over Ga—Cu based supported catalyst, (Physical Chemistry Chemical Physics (2001), 3(21)).*

* cited by examiner

*Primary Examiner* — Jafar Parsa

(74) *Attorney, Agent, or Firm* — D. Scott Hemingway; Hemingway & Hansen, LLP

(57) ABSTRACT

Provided herein are methods for catalytically hydrogenating carbon dioxide to produce oxygenated hydrocarbons and catalysts for use in same.

19 Claims, 7 Drawing Sheets

UTILIZATION AND RECYCLING OF EMITTED CARBON DIOXIDE

This application claims the benefit of U.S. Provisional Application No. 62/262,247, filed Dec. 2, 2015, which is hereby incorporated in its entirety by this reference.

BACKGROUND

The utilization and recycling of emitted carbon dioxide ($CO_2$) in the production of value-added products, such as chemicals or fuel, is of great environmental and economic importance. Although $CO_2$ can be substituted for carbon monoxide in methanol synthesis, this method is challenging due to the high activation of $CO_2$ and substantial energy input. Further, industrial production of methanol and dimethyl ether (DME) from synthetic gas (syngas) over a heterogeneous catalyst is an inefficient two-step process that uses metal-based copper zinc and dehydration of methanol to DME over a ZSM 5 (Zeolite) solid acid catalyst.

SUMMARY

Provided herein are methods for producing oxygenated hydrocarbons from carbon dioxide. The methods comprise combining hydrogen gas and a carbon dioxide containing-gas in a hydrogenation reactor in the presence of a catalyst under conditions for forming a reaction mixture that includes oxygenated hydrocarbons. The catalyst comprises copper (Cu), gallium (Ga), and mesoporous silica.

Also provided are methods of making methanol, dimethyl ether, or both. The methods comprise performing a single step catalytic hydrogenation of carbon dioxide in a reactor to create a reaction mixture (comprising methanol, dimethyl ether, or both) and the hydrogenation catalyst (comprising copper, gallium, and mesoporous silica) and separating methanol, dimethyl ether, or both from the reaction mixture.

Further provided are catalyst compositions that include copper and gallium on a mesoporous silica support.

DETAILED DESCRIPTION

Figure 1:
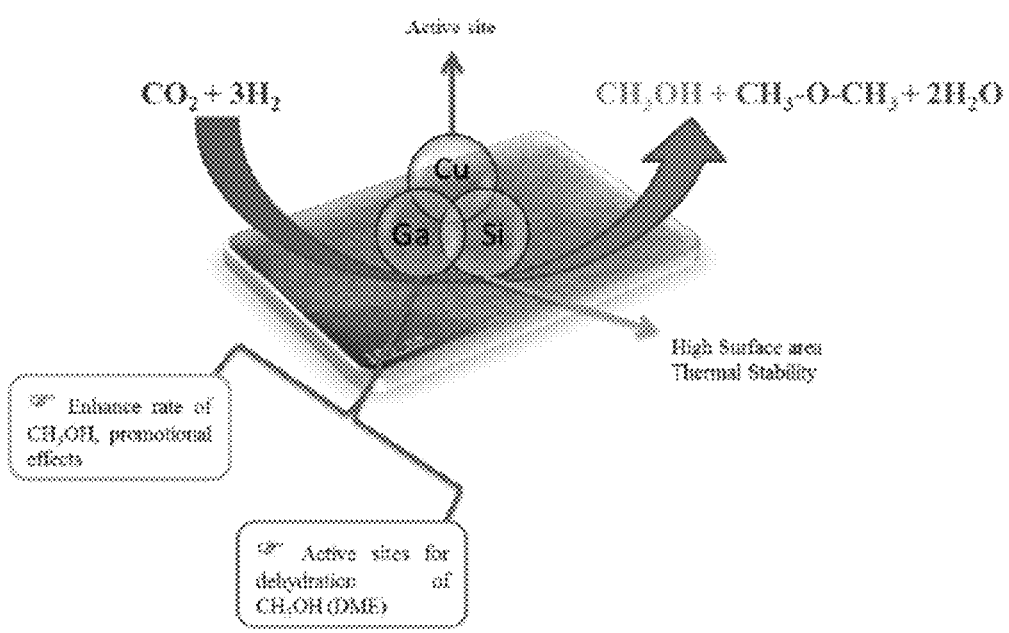
FIG. 1 is a diagram of the production of methanol and dimethyl ether from carbon dioxide by combining carbon dioxide and hydrogen in the presence of a catalyst that includes copper and gallium on a mesoporous silicon support. A gallium-containing catalyst enhances the rate of methanol formation and provides active sites for dehydration of dimethyl ether.

Provided herein are methods for producing oxygenated hydrocarbons from carbon dioxide. Hydrogen gas and a carbon dioxide containing-gas are combined in a hydrogenation reactor in the presence of a catalyst under conditions for forming a reaction mixture. The reaction mixture comprises oxygenated hydrocarbons, and the catalyst comprises copper, gallium, and mesoporous silica. The catalysts possess appropriate basic and acidic characteristics that result in high activity and high selectivity for the single step production of oxygenated hydrocarbons, such as methanol and DME. By using a hydrogenation catalyst comprising copper, gallium, and mesoporous silica, carbon dioxide can be hydrogenated to produce oxygenated hydrocarbons, for example, methanol and dimethyl ether (DME), in a single step hydrogenation reaction. This single step process has substantial advantages over the previous two-step process for industrial production of methanol and DME that involves streaming synthetic gas (syngas) over a metal based catalyst and dehydration of DME over a solid acid catalyst. In the methods provided herein, the catalysts also enhance the rate formation of methanol, efficiently produce DME in a single step without the addition of an acid-co-catalyst and lower the rate of the reverse water gas shift (RWGS) reaction to increase selectivity toward oxygenates.

In the methods provided herein, the process of catalytically hydrogenating carbon dioxide takes place in a reactor. A variety of reactor devices can be used. The reactor includes a reactor vessel configured for containing the catalyst composition and reactants and is equipped with a reactor feed inlet, such as a feed inlet nozzle, for introducing the hydrogen and carbon dioxide-containing gas reactants into the reactor vessel, and a reactor outlet, such as an outlet nozzle, for removing the reaction mixture from the reactor. The reactor can be, but is not limited to, a fixed bed reactor, fluidized bed reactor, a membrane dual-type reactor, an adiabatic reactor or a radial flow reactor. One or more reactors can be used. For example, a series of reactors can be used with or without heat exchange, quenching, or introduction of additional feed material, i.e., carbon dioxide and/or hydrogen. Alternatively, a shell and tube reactor provided with a heat transfer medium can be used. In many cases, the reaction zone can be housed in a single vessel or in a series of vessels with heat exchangers located in between the vessels.

As used throughout, oxygenated hydrocarbons include alcohols and ethers, for example, methanol and DME. In the methods set forth herein, the oxygenated hydrocarbons in the reaction mixture can comprise at least about 70% methanol. For example, the oxygenated hydrocarbons can comprise at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or any percentage in between these percentages. By way of example, methanol in a concentration of about 60-70% (for example, from about 60-71%) and dimethyl ether in a concentration of 30-40% (for example, about 29-40%) is expected when the range of residence time is 0.08-0.24 g/sec at 250° C. over 10Cu5Ga/SBA 15-UDP catalyst.

In any of the methods described herein, the hydrogenation reaction is performed at temperatures of about 175° C. to about 400° C. For example, and not to be limiting, the temperature can be from about 200° C. to about 250° C., from about 200° C. to about 300° C., from about 200° C. to about 350° C., from about 200° C. to about 400° C., from about 225° C. to about 275° C., from about 225° C. to about 300° C., 225° C. to about 350° C., from about 225° C. to about 400° C., from about 250° C. to about 300° C., from about 250° C. to about 250° C., or from about 250° C. to about 400° C.

In any of the methods described herein, the pressure of the hydrogen gas during the hydrogenation reaction is maintained within the range of 1-100 bars, including, for example, at 15-85, 20-80, and about 25 bars.

In any of the methods described herein, the carbon dioxide-containing gas is added to the reactor at a gas hourly space velocity (GHSV or reactant gas flow/reactor volume) of about 4,800 L/Kg×h$^{-1}$ to about 30,000 L/Kg×h$^{-1}$. For example, the carbon-dioxide containing gas can be added at a GHSV of about 4,800 L/Kg×h$^{-1}$, 5,000 L/Kg×h$^{-1}$, 5,200 L/Kg×h$^{-1}$, 5,400 L/Kg×h$^{-1}$, 5,600 L/Kg×h$^{-1}$, 5,800 L/Kg×h$^{-1}$, 6,000 L/Kg×h$^{-1}$, 6,200 L/Kg×h$^{-1}$, 6,400 L/Kg×h$^{-1}$, 6,600 L/Kg×h$^{-1}$, 6,800 L/Kg×h$^{-1}$, 7,000 L/Kg×h$^{-1}$, 7,200 L/Kg×h$^{-1}$, 7,400 L/Kg×h$^{-1}$, 7,600 L/Kg×h$^{-1}$, 7,800 L/Kg×h$^{-1}$, 8,000 L/Kg×h$^{-1}$, 8,200 L/Kg×h$^{-1}$, 8,400 L/Kg×h$^{-1}$, 8,600 L/Kg×h$^{-1}$, 8,800 L/Kg×h$^{-1}$, 9,000 L/Kg×h$^{-1}$, 9,200 L/Kg×h$^{-1}$, 9,400 L/Kg×h$^{-1}$, 9,600 L/Kg×h$^{-1}$, 9,800 L/Kg×h$^{-1}$, 10,000 L/Kg×h$^{-1}$, 10,200 L/Kg×h$^{-1}$, 10,400 L/Kg×h$^{-1}$, 10,600 L/Kg×h$^{-1}$, 10,800 L/Kg×h$^{-1}$, 11,000 L/Kg×h$^{-1}$, 11,200 L/Kg×h$^{-1}$, 11,400 L/Kg×h$^{-1}$, 11,600 L/Kg×h$^{-1}$, 11,800 L/Kg×h$^{-1}$, 12,000 L/Kg×h$^{-1}$, 12,200 L/Kg×h$^{-1}$, 12,400 L/Kg×h$^{-1}$, 12,600 L/Kg×h$^{-1}$, 12,800 L/Kg×h$^{-1}$, 13,000 L/Kg×h$^{-1}$, 13,200 L/Kg×h$^{-1}$, 13,400 L/Kg×h$^{-1}$, 13,600 L/Kg×h$^{-1}$, 13,800 L/Kg×h$^{-1}$, 14,000 L/Kg×h$^{-1}$, 14,200 L/Kg×h$^{-1}$, 14,400 L/Kg×h$^{-1}$, 14,600 L/Kg×h$^{-1}$, 14,800 L/Kg×h$^{-1}$, 15,000 L/Kg×h$^{-1}$, 15,200 L/Kg×h$^{-1}$, 15,400 L/Kg×h$^{-1}$, 15,600 L/Kg×h$^{-1}$, 15,800 L/Kg×h$^{-1}$, 16,000 L/Kg×h$^{-1}$, 16,200 L/Kg×h$^{-1}$, 16,400 L/Kg×h$^{-1}$, 16,600 L/Kg×h$^{-1}$, 16,800 L/Kg×h$^{-1}$, 17,000 L/Kg×h$^{-1}$, 17,200 L/Kg×h$^{-}$, 17,400 L/Kg×h$^{-}$, 17,600 L/Kg×h$^{-1}$, 17,800 L/Kg×h$^{-1}$, 18,000 L/Kg×h$^{-1}$, 18,200 L/Kg×h$^{-1}$, 18,400 L/Kg×h$^{-1}$, 18,600 L/Kg×h$^{-1}$, 18,800 L/Kg×h$^{-1}$, 19,000 L/Kg×h$^{-1}$, 19,200 L/Kg×h$^{-1}$, 19,400 L/Kg×h$^{-1}$, 19,600 L/Kg×h$^{-1}$, 19,800 L/Kg×h$^{-1}$, 20,000 L/Kg×h$^{-1}$, 20,200 L/Kg×h$^{-1}$, 20,400 L/Kg×h$^{-1}$, 20,600 L/Kg×h$^{-1}$, 20,800 L/Kg×h$^{-1}$, 21,000 L/Kg×h$^{-1}$, 21,200 L/Kg×h$^{-1}$, 21,400 L/Kg×h$^{-1}$, 21,600 L/Kg×h$^{-1}$, 21,800 L/Kg×h$^{-1}$, 22,000 L/Kg×h$^{-1}$, 22,200 L/Kg×h$^{-1}$, 22,400 L/Kg×h$^{-1}$, 22,600 L/Kg×h$^{-1}$, 22,800 L/Kg×h$^{-1}$, 23,000 L/Kg×h$^{-1}$, 23,200 L/Kg×h$^{-1}$, 23,400 L/Kg×h$^{-1}$, 23,600 L/Kg×h$^{-1}$, 23,800 L/Kg×h$^{-1}$, 24,000 L/Kg×h$^{-}$, 24,200 L/Kg×h$^{-1}$, 24,400 L/Kg×h$^{-1}$, 24,600 L/Kg×h$^{-1}$, 24,800 L/Kg×h$^{-1}$, 25,000 L/Kg×h$^{-1}$, 25,200 L/Kg×h$^{-1}$, 25,400 L/Kg×h$^{-1}$, 25,600 L/Kg×h$^{-1}$, 25,800 L/Kg×h$^{-1}$, 26,000 L/Kg×h$^{-1}$, 26,200 L/Kg×h$^{-1}$, 26,400 L/Kg×h$^{-1}$, 26,600 L/Kg×h$^{-1}$, 26,800 L/Kg×h$^{-}$, 27,000 L/Kg×h$^{-1}$, 27,200 L/Kg×h$^{-1}$, 27,400 L/Kg×h$^{-1}$, 27,600 L/Kg×h$^{-1}$, 27,800 L/Kg×h$^{-1}$, 28,000 L/Kg×h$^{-1}$, 28,200 L/Kg×h$^{-1}$, 28,400 L/Kg×h$^{-1}$, 28,600 L/Kg×h$^{-1}$, 28,800 L/Kg×h$^{-1}$, 29,000 L/Kg×h$^{-1}$, 29,200 L/Kg×h$^{-1}$, 29,400 L/Kg×h$^{-1}$, 29,600 L/Kg×h$^{-1}$, 29,800 L/Kg×h$^{-1}$, 30,000 L/Kg×h$^{-1}$, or any GHSV in between these velocities.

Alternatively, in any of the methods described herein, the carbon dioxide-containing gas is added to the reactor at a weight hourly space velocity (WHSV or mass flow/catalyst mass) of about 4,800 h$^{-1}$ to about 30,000 h$^{-1}$. For example, the carbon-dioxide containing gas can be added at a WHSV of about 4,800 h$^{-1}$, 5,000 h$^{-1}$, 5,200 h$^{-1}$, 5,400 h$^{-1}$, 5,600 h$^{-1}$, 5,800 h$^{-1}$, 6,000 h$^{-1}$, 6,200 h$^{-1}$, 6,400 h$^{-1}$, 6,600 h$^{-1}$, 6,800 h$^{-1}$, 7,000 h$^{-1}$, 7,200 h$^{-1}$, 7,400 h$^{-1}$, 7,600 h$^{-1}$, 7,800 h$^{-1}$, 8,000 h$^{-1}$, 8,200 h$^{-1}$, 8,400 h$^{-1}$, 8,600 h$^{-1}$, 8,800 h$^{-1}$, 9,000 h$^{-1}$, 9,200 h$^{-1}$, 9,400 h$^{-1}$, 9,600 h$^{-1}$, 9,800 h$^{-1}$, 10,000 h$^{-1}$, 10,200 h$^{-1}$, 10,400 h$^{-1}$, 10,600 h$^{-1}$, 10,800 h$^{-1}$, 11,000 h$^{-1}$, 11,200 h$^{-1}$, 11,400 h$^{-1}$, 11,600 h$^{-1}$, 11,800 h$^{-1}$, 12,000 h$^{-1}$, 12,200 h$^{-1}$, 12,400 h$^{-1}$, 12,600 h$^{-1}$, 12,800 h$^{-1}$, 13,000 h$^{-1}$, 13,200 h$^{-1}$, 13,400 h$^{-1}$, 13,600 h$^{-1}$, 13,800 h$^{-1}$, 14,000 h$^{-1}$, 14,200 h$^{-1}$, 14,400 h$^{-1}$, 14,600 h$^{-1}$, 14,800 h$^{-1}$, 15,000 h$^{-1}$, 15,200 h$^{-1}$, 15,400 h$^{-1}$, 15,600 h$^{-1}$, 15,800 h$^{-1}$, 16,000 h$^{-1}$, 16,200 h$^{-1}$, 16,400 h$^{-1}$, 16,600 h$^{-1}$, 16,800 h$^{-1}$, 17,000 h$^{-1}$, 17,200 h$^{-1}$, 17,400 h$^{-1}$, 17,600 h$^{-1}$, 17,800 h$^{-1}$, 18,000 h$^{-1}$, 18,200 h$^{-1}$, 18,400 h$^{-1}$, 18,600 h$^{-1}$, 18,800 h$^{-1}$, 19,000 h$^{-1}$, 19,200 h$^{-1}$, 19,400 h$^{-1}$, 19,600 h$^{-1}$, 19,800 h$^{-1}$, 20,000 h$^{-1}$, 20,200 h$^{-1}$, 20,400 h$^{-1}$, 20,600 h$^{-1}$, 20,800 h$^{-1}$, 21,000 h$^{-1}$, 21,200 h$^{-1}$, 21,400 h$^{-1}$, 21,600 h$^{-1}$, 21,800 h$^{-1}$, 22,000 h$^{-1}$, 22,200 h$^{-1}$, 22,400 h$^{-1}$, 22,600 h$^{-1}$, 22,800 h$^{-1}$, 23,000 h$^{-1}$, 23,200 h$^{-1}$, 23,400 h$^{-1}$, 23,600 h$^{-1}$, 23,800 h$^{-1}$, 24,000 h$^{-1}$, 24,200 h$^{-1}$, 24,400 h$^{-1}$, 24,600 h$^{-1}$, 24,800 h$^{-1}$, 25,000 h$^{-1}$, 25,200 h$^{-1}$, 25,400 h$^{-1}$, 25,600 h$^{-1}$, 25,800 h$^{-1}$, 26,000 h$^{-1}$, 26,200 h$^{-1}$, 26,400 h$^{-1}$, 26,600 h$^{-1}$, 26,800 h$^{-1}$, 27,000 h$^{-1}$, 27,200 h$^{-1}$, 27,400 h$^{-1}$, 27,600 h$^{-1}$, 27,800 h$^{-1}$, 28,000 h$^{-1}$, 28,200 h$^{-1}$, 28,400 h$^{-1}$, 28,600 h$^{-1}$, 28,800 h$^{-1}$, 29,000 h⁻¹, 29,200 h⁻¹, 29,400 h⁻¹, 29,600 h⁻¹, 29,800 h⁻¹, 30,000 h⁻¹ or any WHSV in between these velocities.

In any of the methods described herein, the ratio of carbon dioxide to hydrogen in the reactor is about 3:1 by volume. This is achieved by passing or streaming about 3 volumes of carbon dioxide-containing gas per volume of hydrogen gas through a hydrogenation zone that is in contact with a hydrogenation catalyst in the reactor. Carbon dioxide and hydrogen are optionally charged separately into the reactor so as to reach the desired ratio by volume in the reactor. Alternatively, the carbon dioxide and hydrogen can be mixed to the desired ratio prior to addition to the reactor as described below.

Hydrogen and a carbon dioxide-containing gas can be mixed in conventional mixing devices prior to introducing or feeding of the mixture of hydrogen gas and carbon dioxide gas into the reactor. The $H_2/CO_2$ molar ratio in the mixed gas is optionally to the range desired in the reactor.

The ratio of carbon dioxide to hydrogen in the reactor is selected from the group consisting of 1:3, 1:4, 1:5, 1:6, 1:7, 1:19 or 1:10. By way of example, a ratio of carbon dioxide to hydrogen of 1:3 can be achieved prior to introduction of the mixture into the reactor or can be achieved by adding the components separately to the reactor.

Both gases are readily available as industrial by-products from a number of processes. Thus, carbon dioxide is present in a number of synthetic gas mixtures as a result of gasification of hydrocarbons or coal and is separated therefrom by conventional removal methods, such as scrubbing, pressure swing adsorption and cryogenic separation methods. Carbon dioxide can also be removed from the atmosphere or from the ocean. Hydrogen is commonly obtained as a by-product from a purge gas from petrochemical or ammonia plants by recovery in cryogenic separation, and used as fuel in those plants. Therefore, there are numerous sources from which hydrogen and a carbon dioxide-containing gas can be obtained These gases can be captured, stored and/or processed prior to being introduced into the reactor. Carbon dioxide sequestration and capture technologies that allow separation of carbon dioxide from process streams for further storage or recycling are known in the art.

The methods of producing oxygenated hydrocarbons can further comprise separating one or more oxygenated hydrocarbons from the reaction mixture to form a hydrocarbon-depleted reaction mixture. For example, the methods can comprise separating methanol and/or DME from the reaction mixture. Any of the hydrocarbons removed from the reaction mixture can be further processed into other products, such as fuels or chemicals. As used herein, a hydrocarbon-depleted reaction mixture is a reaction mixture in which all or most of the oxygenated hydrocarbons have been removed. For example, a hydrocarbon-depleted reaction mixture can comprise less than about 1% oxygenated hydrocarbons. The effluent of the reactor (reaction mixture) is cooled to separate dimethyl ether, methanol and water from unreacted gas, and the remaining carbon dioxide and hydrogen are optionally recycled to the reactor.

Further provided is a method of making methanol, dimethyl ether, or both, comprising performing a single step catalytic hydrogenation of carbon dioxide in a reactor to create a reaction mixture, which comprises methanol, dimethyl ether, or both, and a hydrogenation catalyst that comprises copper, gallium, and mesoporous silica. The method further comprises separating methanol, dimethyl ether, or both from the reaction mixture. Optionally, the method further comprises purifying the methanol, dimethyl either, or both. Dimethyl ether is optionally purified in two distillation columns and stored in a pressurized tank. Methanol and water can be separated by a distillation column.

As used herein, a catalyst is a substance that increases the rate of the chemical reaction between molecular hydrogen ($H_2$) and carbon dioxide to selectively produce oxygenated hydrocarbons, in particular, methanol and DME. As such, the catalysts provided herein are hydrogenation catalysts. These hydrogenation catalysts comprise copper, gallium, and mesoporous silica. Therefore, provided herein are catalyst compositions comprising copper, gallium, and mesoporous silica. By way of example, the catalyst comprises a copper gallium catalyst with 5 to 15% copper and 2-10% gallium for the hydrogenation process. The synthesis of the catalyst is performed by various techniques such as wet impregnation and urea deposition methods. Optionally, the compositions comprise a copper gallium catalyst on a mesoporous silica support. The mesoporous silica supports (e.g., SBA 15, MCM 41 and zeolites having various Si—Al ratio) optionally have surface area in the range of 300 to 1500 m²/g with pore volume 0.2-1.8 CC/g and a copper gallium catalyst.

Optionally, copper as used in the catalyst is in the form of copper oxide and gallium is in the form of gallium oxide. Optionally, the catalyst can comprise about 4% to about 15% (w/w) copper. For example, the catalyst can comprise from about 4% to about 5% copper, from about 4% to about 6% copper, from about 4% to about 7% copper, from about 4% to about 8% copper, from about 4% to about 9% copper, from about 4% to about 10% copper, from about 4% to about 11% copper, from about 4% to about 12% copper, from about 4% to about 13% copper, from about 4% to about 14% copper, from about 4% to about 15% copper, from about 5% to about 6% copper, from about 5% to about 7% copper, from about 5% to about 8% copper, from about 5% to about 9% copper, from about 5% to about 10% copper, from about 5% to about 11% copper, from about 5% to about 12% copper, from about 5% to about 13% copper, from about 5% to about 14% copper, from about 5% to about 15% copper, from about 6% to about 7% copper, from about 6% to about 8% copper, from about 6% to about 9% copper, from about 6% to about 10% copper, from about 6% to about 11% copper, from about 6% to about 12% copper, from about 6% to about 13% copper, from about 6% to about 14% copper, from about 6% to about 15% copper, from about 7% to about 8% copper, from about 7% to about 9% copper, from about 7% to about 10% copper, from about 7% to about 11% copper, from about 7% to about 12% copper, from about 7% to about 13% copper, from about 7% to about 14% copper, from about 7% to about 15% copper, from about 8% to about 9% copper, from about 8% to about 10% copper, from about 8% to about 11% copper, from about 8% to about 12% copper, from about 8% to about 13% copper, from about 8% to about 14% copper, from about 8% to about 15% copper, from about 9% to about 10% copper, from about 9% to about 11% copper, from about 9% to about 12% copper, from about 9% to about 13% copper, from about 9% to about 14% copper, from about 9% to about 15% copper, from about 10% to about 11% copper, from about 10% to about 12% copper, from about 10% to about 13% copper, from about 10% to about 14% copper, from about 10% to about 15% copper, from about 11% to about 12% copper, from about 11% to about 13% copper, from about 11% to about 14% copper, from about 11% to about 15% copper, from about 12% to about 13% copper, from about 12% to about 14% copper, from about 12% to about 15% copper, from about 13% to about 14% copper, from about 13% to about 15% copper or from about 14% to about 15% copper.

Optionally, the catalyst can comprise about 2% to about 10% (w/w) gallium. For example, the catalyst can comprise from about 2% to about 3% gallium, from about 2% to about 4% gallium, from about 2% to about 5% gallium, from about 2% to about 6% gallium, from about 2% to about 7% gallium, from about 2% to about 8% gallium, from about 2% to about 9% gallium, from about 2% to about 10% gallium, from about 3% to about 4% gallium, from about 3% to about 5% gallium, from about 3% to about 6% gallium, from about 3% to about 7% gallium, from about 3% to about 8% gallium, from about 3% to about 9% gallium, from about 3% to about 10% gallium, from about 4% to about 5% gallium, from about 4% to about 6% gallium, from about 4% to about 7% gallium, from about 4% to about 8% gallium, from about 4% to about 9% gallium, from about 4% to about 10% gallium, from about 5% to about 6% gallium, from about 5% to about 7% gallium, from about 5% to about 8% gallium, from about 5% to about 9% gallium, from about 5% to about 10% gallium, from about 6% to about 7% gallium, from about 6% to about 8% gallium, from about 6% to about 9% gallium, from about 6% to about 10% gallium, from about 7% to about 8% gallium, from about 7% to about 9% gallium, from about 7% to about 10% gallium, from about 8% to about 9% gallium, from about 8% to about 10% gallium or from about 9% to about 10% gallium.

Any of the catalyst compositions described herein can be used in any of the methods for catalytic hydrogenation provided herein. The catalyst can be a powder for use as a fixed-bed catalyst or can be used in pellet or tablet form.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compositions may not be explicitly disclosed, each is specifically contemplated and described herein. For example, if a method is disclosed and discussed and a number of modifications that can be made to a number of compositions including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

EXAMPLES

Using the method set forth herein, methanol and dimethyl ether were produced upon catalytic hydrogenation of carbon dioxide in the presence of a catalyst comprising copper, gallium and mesoporous silica. As shown in FIG. 1, the gallium-containing catalyst produces methanol and DME while enhancing the rate of methanol formation. Various hydrogenation catalysts comprising copper and gallium on a SBA-15 support were made (4Cu2GA/SBA-15UDP, 10Cu5GA/SBA-15UDP, 16Cu10GA/SBA-15Imp) as well as with a catalyst comprising copper and zinc on SBA-15 support (17Cu13Zn/SBA-15Imp). As shown in Table 1, combining carbon dioxide and hydrogen in the presence of a gallium-containing hydrogenation catalyst resulted in selective production of methanol and DME. The rate of methanol formation was also enhanced. In contrast, combining carbon dioxide and hydrogen in the presence of the copper/zinc catalyst did not result in selective production of methanol and DME.

Synthesis of Catalysts

Both 4Cu2Ga/SBA-15UDP and 10Cu5Ga/SBA-15UDP catalysts were prepared using a urea deposition method. For 4Cu2Ga/SBA-15UDP, the synthesis was performed by suspending copper nitrate (0.28 g), gallium nitrate (0.18 g), and urea (1.5 g) in aqueous medium (100 ml). For 10Cu5Ga/SBA-15UDP, the synthesis was performed by suspending copper nitrate (0.57 g), gallium nitrate (0.36 g), and urea (2.8 g) in aqueous medium (100 ml). In each case, 0.5 g of calcined SBA-15 were added slowly to the suspension and the mixture was heated at 90° C. for 8 h. The catalyst was filtered and dried at 120° C. for 12 h and calcined at 450° C. for 8 h. It was then subsequently reduced using 5% $H_2$/Ar (5 mL/min) in a fixed bed reactor for 12 h.

Catalysts 10Cu/SBA15IMP, 16Cu10Ga/SBA15IMP and 17Cu13Zn/SBA15IMP were prepared using a wet impregnation method. (3) 10Cu/SBA-15Imp: Supported monometallic copper catalyst was synthesized by suspending 0.5 g of SBA-15 in aqueous medium with copper nitrate (0.57 g). The suspension was stirred for 8 h at room temperature. Water was removed. The resulting solid was dried at 120° C. for 12 h, calcined at 450° C. for 8 h, and subsequently reduced using 5% $H_2$/Ar (5 mL/min) in a fixed bed reactor for 12 h.

For 16Cu10Ga/SBA-15Imp, supported copper and gallium catalyst was prepared by suspending 0.5 g of SBA-15 in aqueous medium with copper nitrate (0.57 g) and gallium nitrate (0.36 g). The suspension was stirred for 8 h at room temperature. Water was removed and the resulting solid dried, calcined, and reduced as for catalysts 10Cu/SBA15-IMP, 16Cu10Ga/SBA15-IMP and 17Cu13Zn/SBA 15-UDP.

For 17Cu13Zn/SBA15-Imp, supported copper and zinc catalyst was prepared by suspending 0.5 g of SBA-15 in aqueous medium with copper nitrate (0.57 g) and zinc nitrate (0.45 g). The suspension was stirred for 8 h at room temperature. Water was removed and the resulting solid dried, calcined, and reduced as for catalysts 10Cu/SBA15-IMP, 16Cu10Ga/SBA15-IMP and 17Cu13Zn/SBA15IMP.

Reactor Set Up and Conditions

The catalytic tests were performed in a fixed-bed continuous flow dynamic reactor. In a typical experiment, 50-250 mg of the prepared catalyst with inert carborundum (950-750 mg) was loaded into the reactor. The purity of gases used for reaction feed ($CO_2$ and $H_2$) was greater than 99.99% and the gases used for the reactions were dehydrated and purified with suitable filters. After loading the catalyst to the reactor, the catalyst was reduced at 250° C. in a flow of 5 mL/min of 5% $H_2$/Ar for 12 h and then cooled to room temperature. The reaction was then heated to 250° C. with a rate of 50° C./min and the feed flow of 25 mL/min passed through the reactor having a weight hourly space velocity in the range of 4800 to 30000 L/g·h with the increase of $CO_2$ and $H_2$ pressure to 25 bar. A stream of outlet gas tube was placed at the outside of the dynamic reactor, which was used to constantly sample the outlet gas to the gas chromatogram (GC) (equipped with a thermal conductivity detector (TCD) and flame ionization detector (FIDs).

Reaction conditions in the reactor were as follows: T=250° C., P=25 bar, Gas Flow $(CO_2/Ar/H_2)$=5/5/15 ml/min, GHSV (Gas hourly space velocity) 30000 $h^{-1}$, $CO_2/H_2$=1:3, Time=24 h. $CO_2$ conversion was determined directly from the carbon balance. Data are shown in Table 1.

TABLE 1

Activity on hydrogenation $CO_2$ to Oxygenates

| Catalyst | Conversion (%) | Carbon Balance (%) | Selectivity (%) | | |
|---|---|---|---|---|---|
| | | | $CH_3OH$ | CO | DME |
| 10Cu5Ga/SBA-15UDP | 3 | 99.95 | 71 | <0.01 | 29 |
| 4Cu2Ga/SBA-15UDP | 2 | 99.95 | 73 | <0.01 | 27 |
| 10Cu/SBA-15Imp | 0.045 | 100 | 99.9 | <0.01 | <0.01 |
| 16Cu10Ga/SBA-15Imp | 1 | 99.96 | 78 | <0.01 | 22 |
| 17Cu13Zn/SBA-15 Imp | 1 | 99.98 | 99.9 | <0.01 | <0.01 |

Figure 2A:
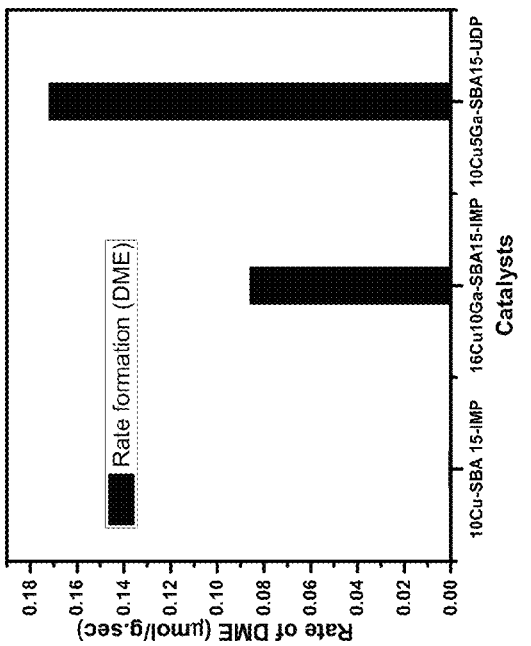
FIG. 2A shows the rates of methanol formation via hydrogenation of carbon dioxide in the presence of 10Cu/SBA-15Imp, 16Cu10Ga/SBA 15Imp, and 10Cu5Ga/SBA 15-UDP as catalysts. Methanol formation rate increased with the incorporation of Ga into Cu/SBA15 catalysts.
Figure 2B:
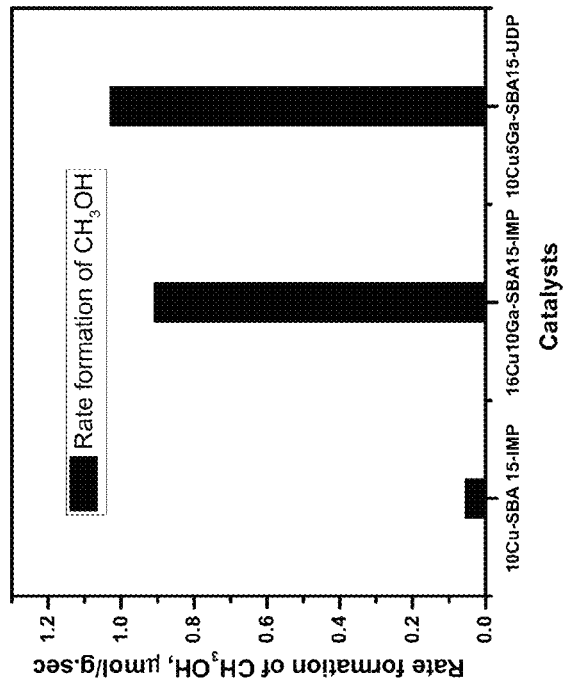
FIG. 2B shows enhancement of DME formation rate with 10Cu/SBA-15Imp, 16Cu10Ga/SBA 15Imp, and 10Cu5Ga/SBA 15-UDP.

FIG. 2A shows the rates of methanol formation via hydrogenation of carbon dioxide in the presence of 10Cu/SBA-15Imp, 16Cu10Ga/SBA 15Imp, and 10Cu5Ga/SBA 15-UDP, showing that the methanol formation rate increased with the incorporation of Ga to Cu/SBA15 catalysts. FIG. 2B shows a similar trend in the enhancement of the DME formation rate with the same series of catalysts.

Figure 3:
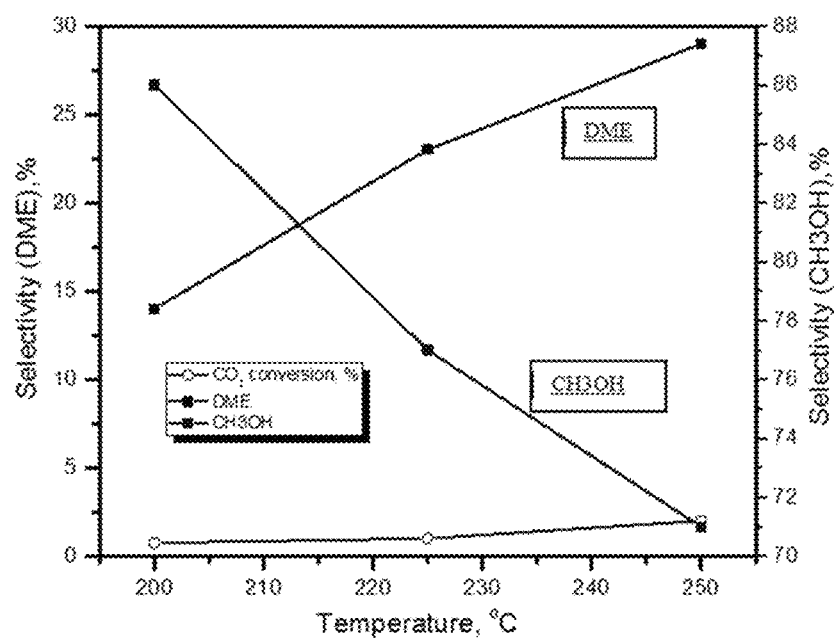
FIG. 3 shows the effects of temperature on $CO_2$ hydrogenation. Hydrogenation of carbon dioxide in the presence of 10Cu5Ga/SBA 15-UDP results in conversion of $CO_2$ to methanol and dimethyl ether (DME). However, as temperature is increased from 200-250° C., conversion of $CO_2$ to dimethyl ether is enhanced. The reaction conditions were as follows: T=200-250° C., P=25 bar, Gas Flow ($CO_2$/Ar/$H_2$)=5/5/15 ml/min, weight hourly space velocity (WHSV) 30000 $h^{-1}$, $CO_2$/$H_2$=1:3, Time=12 h.

The effect of temperature on $CO_2$ hydrogenation was also determined. The reaction conditions were as follows: T=200-250° C., P=25 bar, Gas Flow $(CO_2/Ar/H_2)$=5/5/15 ml/min, WHSV (Weight hourly space velocity) 30000 $h^{-1}$, $CO_2/H_2$=1:3, Time=12 h. As shown in FIG. 3, hydrogenation of carbon dioxide in the presence of 10Cu5Ga/SBA 15-UDP results in conversion of $CO_2$ to methanol and dimethyl ether. However, as temperature is increased from 200-250° C., conversion of $CO_2$ to dimethyl ether is enhanced.

Figure 4:
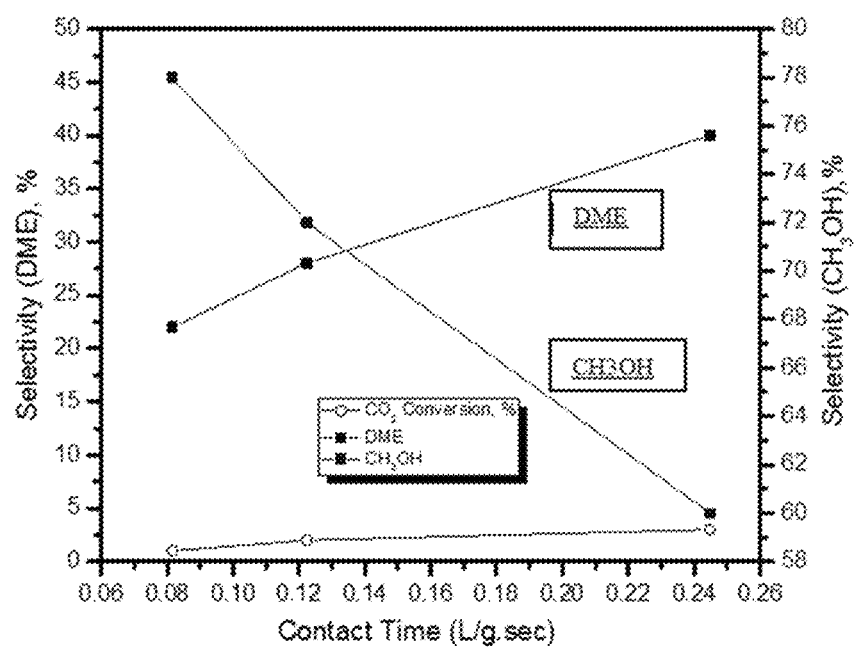
FIG. 4 shows the effect of catalyst time vs. feed flow on $CO_2$ hydrogenation. Hydrogenation of carbon dioxide in the presence of 10Cu5Ga/SBA 15-UDP results in conversion of $CO_2$ to methanol and dimethyl ether. However, as contact time increases, conversion of $CO_2$ to dimethyl ether is enhanced. The reaction conditions were as follows: T=250° C., P=25 bar, Gas Flow ($CO_2$/Ar/$H_2$)=2.5/2.5/7.5, 5/5/15, 7.5/7.5/22.5 ml/min, WHSV 30000 $h^{-1}$, $CO_2$/$H_2$=1:3, Time=24 h.

The effect of catalyst contact time vs. feed flow on $CO_2$ hydrogenation was also determined. The reaction conditions were as follows: T=250° C., P=25 bar, Gas Flow $(CO_2/Ar/H_2)$=2.5/2.5/7.5, 5/5/15, 7.5/7.5/22.5 ml/min, WHSV 30000 $h^{-1}$, $CO_2/H_2$=1:3, Time=24 h. As shown in FIG. 4, hydrogenation of carbon dioxide in the presence of 10Cu5Ga/SBA 15-UDP results in conversion of $CO_2$ to methanol and dimethyl ether. However, as contact time increases conversion of $CO_2$ to dimethyl ether is enhanced.

Figure 5:
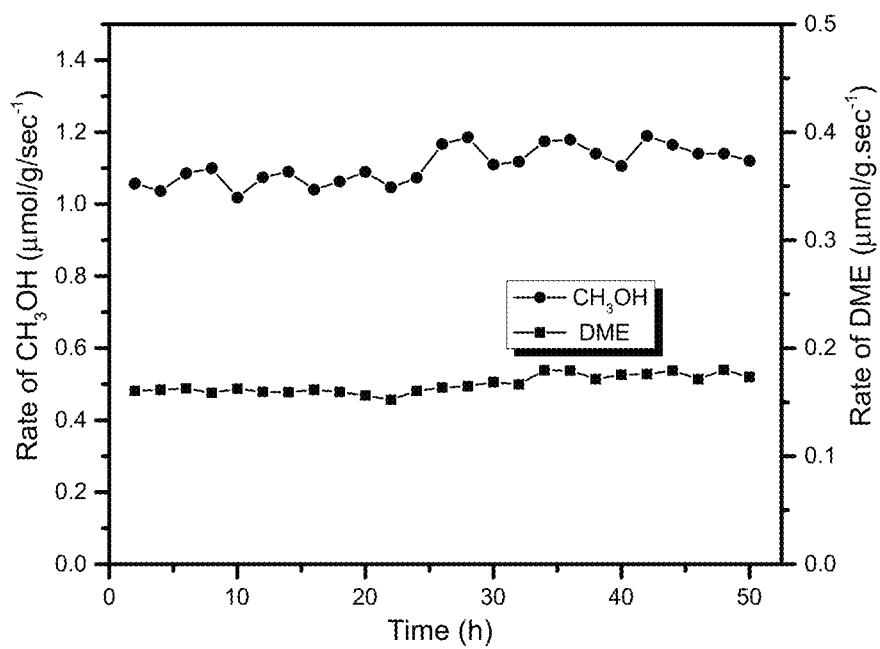
FIG. 5 shows the effect of time on stream activity on $CO_2$ hydrogenation. The rate of conversion of methanol and dimethyl ether are shown. Consistent formation rates of methanol (1.045 μmol/g·sec) and dimethyl ether (0.167 μmol/g·sec) over a total period of 50 h were observed. >99% of selectivity to oxygenates (methanol and dimethyl ether) was achieved. The reaction conditions were as follows: T=250° C., P=25 bar, Gas Flow ($CO_2$/Ar/$H_2$)=5/5/15 ml/min, GHSV 30000 $h^{-1}$, $CO_2$/$H_2$=1:3, Time=24 h.

The effect of time on stream activity for $CO_2$ hydrogenation was also determined for 10Cu5Ga/SBA 15-UDP. The reaction conditions were as follows: T=250° C., P=25 bar, Gas Flow $(CO_2/Ar/H_2)$=5/5/15 ml/min, GHSV 30000 $h^{-1}$, $CO_2/H_2$=1:3, Time=24 h. The rate of conversion of methanol and dimethyl ether are shown in FIG. 5. Consistent formation rates of methanol (1.045 µmol/g·sec) and dimethyl ether (0.167 µmol/g·sec) over a total period of 50 h were observed. >99% of selectivity to oxygenates (methanol and dimethyl ether) was achieved.

Figure 6:
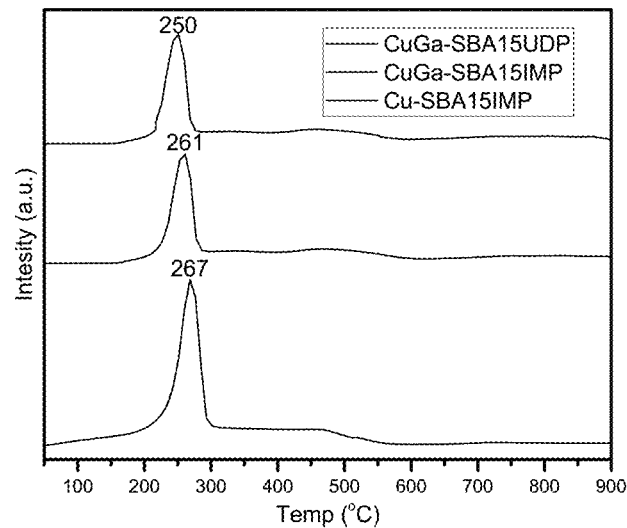
FIG. 6 shows the characterization of several catalysts in $H_2$ temperature-programmed reduction studies. The catalysts were characterized using an Altamira Instrument (AMI-200Ip) equipped with a TCD detector. Temperatures at which a reduction resulting in hydrogen consumption was observed for 10Cu5Ga/SBA-15UDP (upper plot), 16Cu10Ga/SBA-15Imp (middle plot) and 10Cu/SBA-15Imp (lower plot) are shown. The addition of Ga lowers the reduction temperature of the catalyst.

Several catalysts were characterized in $H_2$ temperature-programmed reduction studies using an Altamira Instrument (AMI-200Ip) equipped with a TCD detector. Temperatures at which a reduction resulting in hydrogen consumption was observed for 10Cu5Ga/SBA-15UDP, 16Cu10Ga/SBA-15Imp and 10Cu/SBA-15Imp are shown in FIG. 6. The addition of Ga lowers the reduction temperature of the catalyst.

Figure 7:
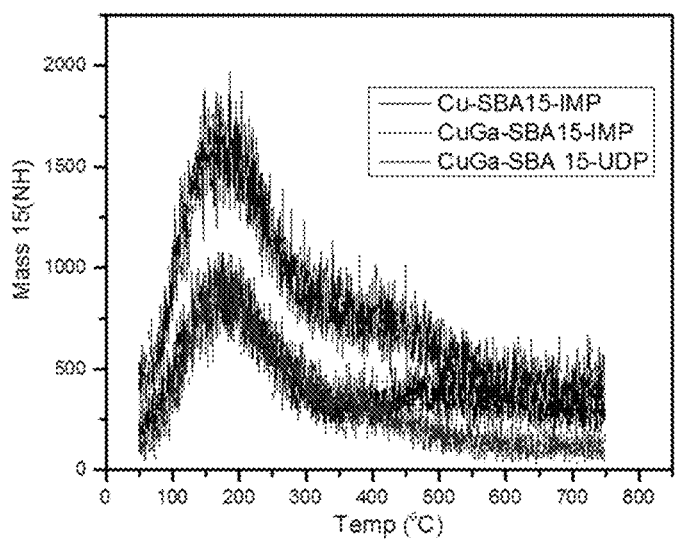
FIG. 7 shows the results of thermodesorption of $NH_3$ in the presence of 10Cu5Ga/SBA-15UDP, 16Cu10Ga/SBA-15Imp and 10Cu/SBA-15Imp as determined using an Altamira Instrument. Addition of Ga increases the acid strength to offer stronger acid sites than the monometallic copper catalyst.

As shown in FIG. 7, the thermodesorption of $NH_3$ in the presence of 10Cu5Ga/SBA-15UDP, 16Cu10Ga/SBA-15Imp and 10Cu/SBA-15Imp was also determined by using an Altamira Instrument. Addition of Ga increases the acid strength to offer stronger acid sites than the monometallic copper catalyst.

Figure 8:
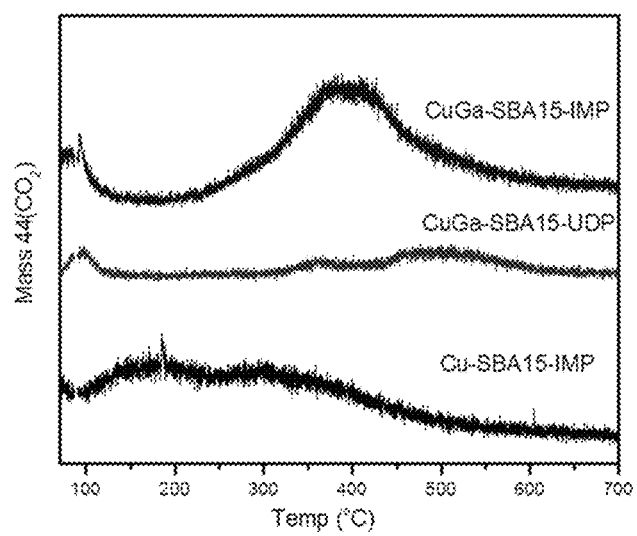
FIG. 8 shows the results of thermodesorption of $CO_2$ in the presence of 10Cu5Ga/SBA-15UDP, 16Cu10Ga/SBA-15Imp and 10Cu/SBA-15Imp. The incorporation of gallium to copper catalysts also increases the basic sites more than those of monometallic copper.

Additionally, as shown in FIG. 8, the thermodesorption of $CO_2$ in the presence of 10Cu5Ga/SBA-15UDP, 16Cu10Ga/SBA-15Imp and 10Cu/SBA-15Imp was determined. The incorporation of gallium into copper catalysts also increases the basic sites more than those of monometallic copper.

Figure 9:
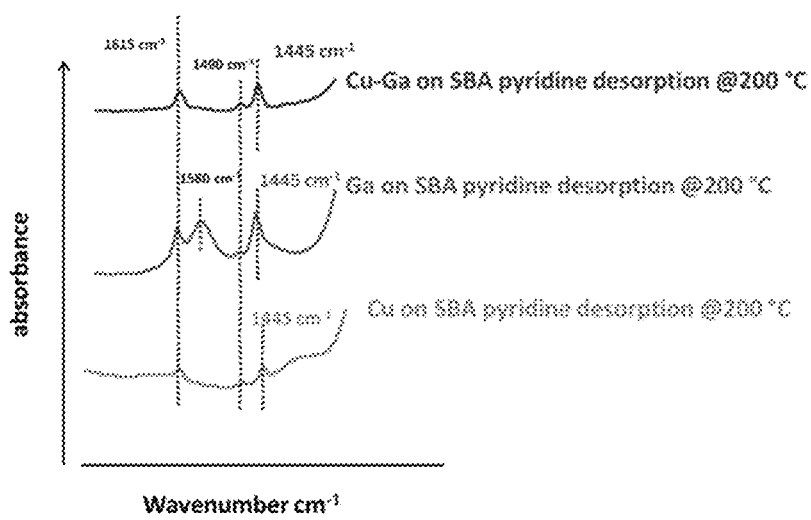
FIG. 9 shows the results of pyridine desorption (PYIR) studies. These studies were also conducted at 200° C. using 10Cu5Ga/SBA-15UDP, 10Cu/SBA-15Imp and 5Ga/SBA-15Imp as catalysts on a Nicolet FT-IR 6700 spectrometer equipped with an DTGS-KBr detector at a 16 $cm^{-1}$ resolution with 32 scans for each spectrum. Strong Lewis acid sites were observed in 5Ga/SBA15 and 10Cu5Ga/SBA15.

As shown in FIG. 9, pyridine desorption (PYIR) studies were also conducted at 200° C. using 10Cu5Ga/SBA-15UDP, 10Cu/SBA-15Imp and 5Ga/SBA-15Imp on a Nicolet FT-IR 6700 spectrometer equipped with an DTGS-KBr detector at a 16 $cm^{-1}$ resolution with 32 scans for each spectrum. Strong Lewis acid sites were observed in 5Ga/SBA15 and 10Cu5Ga/SBA15.

What is claimed is:

1. A method for producing oxygenated hydrocarbons from carbon dioxide comprising combining hydrogen gas and a carbon dioxide containing-gas in a hydrogenation reactor in the presence of a catalyst under conditions for forming a reaction mixture comprising oxygenated hydrocarbons, wherein the catalyst comprises copper, gallium, and mesoporous silica.

2. The method of claim 1, further comprising separating one or more oxygenated hydrocarbons from the reaction mixture to form a hydrocarbon-depleted reaction mixture.

3. The method of claim 2, further comprising recycling the hydrocarbon-depleted reaction mixture to the reactor.

4. The method of claim 1 or 2, wherein the catalyst is a fixed-bed catalyst.

5. The method of claim 1, wherein the pressure of the hydrogen gas is maintained at about 25 bar.

6. The method of claim 1, wherein the ratio of carbon dioxide to hydrogen in the reactor is about 3:1 by volume.

7. The method of claim 1, wherein the temperature in the hydrogenation reactor is maintained in the range of about 200° C. to about 300° C.

8. The method of claim 1, wherein the carbon dioxide-containing gas is added to the reactor at a gas hourly space velocity (GHSV) of about 4,800 L/Kg×$h^{-1}$ to about 30,000 L/Kg×$h^{-1}$.

9. The method of claim 1, wherein the catalyst comprises about 4% to about 15% (w/w) copper.

10. The method of claim 9, wherein the copper is in the form of copper oxide.

11. The method of claim 1, wherein the catalyst comprises about 2% to about 10% (w/w) gallium.

12. The method of claim 11, wherein the gallium is in the form of gallium oxide.

13. The method of claim 1, wherein the mesoporous silica acts as a support for the copper and gallium.

14. The method of claim 1, wherein the oxygenated hydrocarbons comprise methanol and dimethyl ether.

15. The method of claim 1, wherein the oxygenated hydrocarbons in the reaction mixture comprise at least about 90% methanol.

16. The method of claim 1, wherein the method comprises a single step of hydrogenation.

17. The method of claim 1, wherein the method lacks a co-catalyst.

18. A method of making methanol, dimethyl ether, or both, comprising
  a. performing a single step catalytic hydrogenation of carbon dioxide in a reactor to create a reaction mixture comprising methanol, dimethyl ether, or both, wherein the hydrogenation catalyst comprises copper, gallium, and mesoporous silica, and b. separating methanol, dimethyl ether, or both from the reaction mixture.

19. The method of claim 18, further comprising purifying the methanol, dimethyl ether, or both.

* * * * *